United States Patent [19]

Storace

[11] Patent Number: 4,691,853

[45] Date of Patent: Sep. 8, 1987

[54] SURGICAL STAPLER

[75] Inventor: Anthony Storace, Norwalk, Conn.

[73] Assignee: Technalytics, Inc., Montvale, N.J.

[21] Appl. No.: 814,666

[22] Filed: Dec. 30, 1985

[51] Int. Cl.⁴ .............................................. A61B 17/00
[52] U.S. Cl. ........................................ 227/19; 72/409;
128/334 R; 227/120; 227/DIG. 1; 227/119;
227/116
[58] Field of Search ............. 72/409, 410; 128/334 R;
227/19, 120, DIG. 1, 107, 114, 115, 116, 117,
119

[56]  References Cited
U.S. PATENT DOCUMENTS

| | | | |
|---|---|---|---|
| 1,977,282 | 10/1934 | Kruse | 72/410 |
| 2,086,922 | 7/1937 | Peterson | 227/119 X |
| 2,231,539 | 2/1941 | Larsen | 227/116 |
| 3,180,128 | 4/1965 | Faulkner | 72/409 |
| 4,185,762 | 1/1980 | Froehlich | 227/19 X |
| 4,396,139 | 8/1983 | Hall et al. | 227/19 |
| 4,478,362 | 10/1984 | Foslien | 227/DIG. 1 |
| 4,527,725 | 7/1985 | Foslien | 227/19 |
| 4,592,498 | 6/1986 | Braun et al. | 227/DIG. 1 |
| 4,596,350 | 6/1986 | Smith et al. | 227/DIG. 1 |

Primary Examiner—Paul A. Bell
Attorney, Agent, or Firm—Curtis, Morris & Safford

[57]  ABSTRACT

A surgical stapler device of the so-called pistol grip type includes a stack of staples loaded into a lower cartridge in an orientation similar to a conventional paper stapler. A former rotates and turns a leading staple 90° or normal to its prior orientation in the stack of staples as the former slides between a start position and an intermediate position. The rotational movement of the staple insures maximum clarity in the surgeon's line of visions when placing a staple in position. The former is further displaced between an intermediate and a final position wherein the staple is formed around a staple forming surface of an anvil. The former also cams the anvil downwardly separating the formed staple from the anvil lip, thereby allowing the former to receive a staple from the stack of staples onto its staple transport surface for sequential stapling.

41 Claims, 16 Drawing Figures

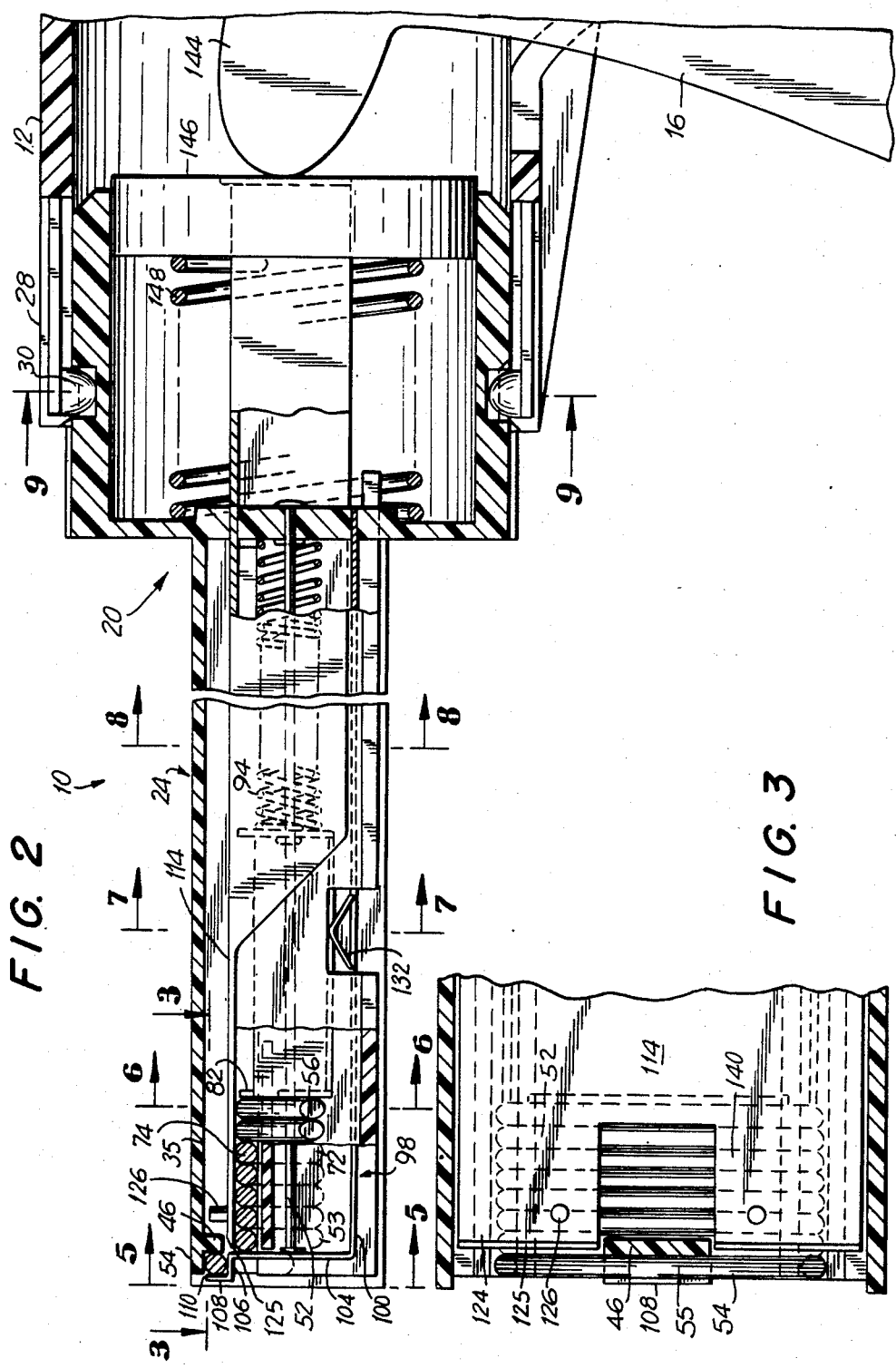

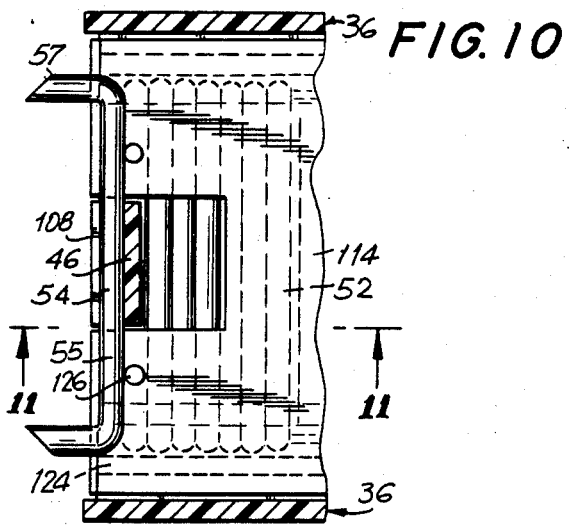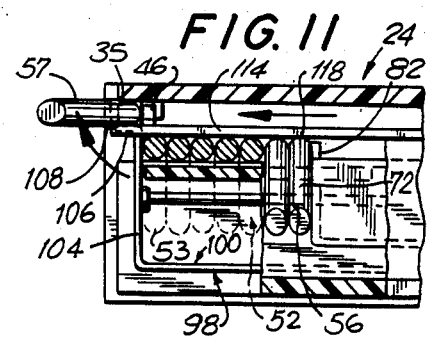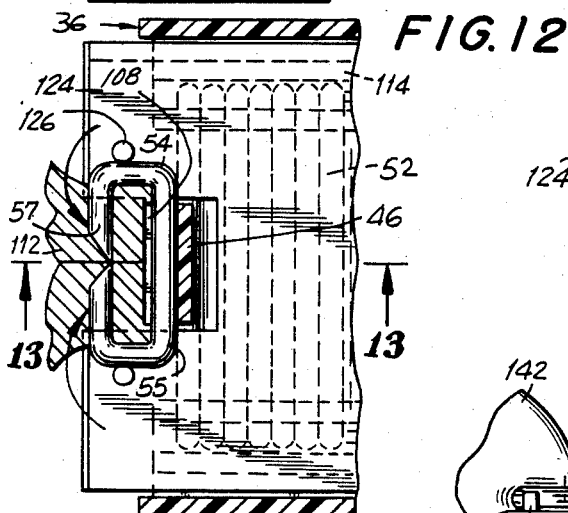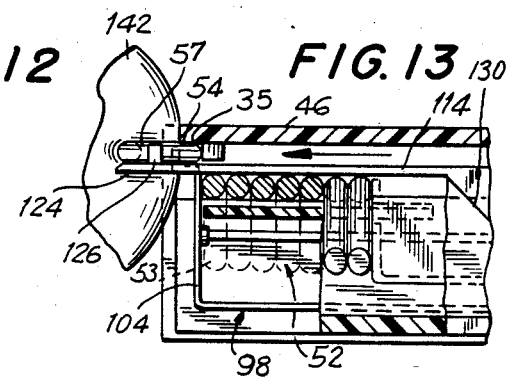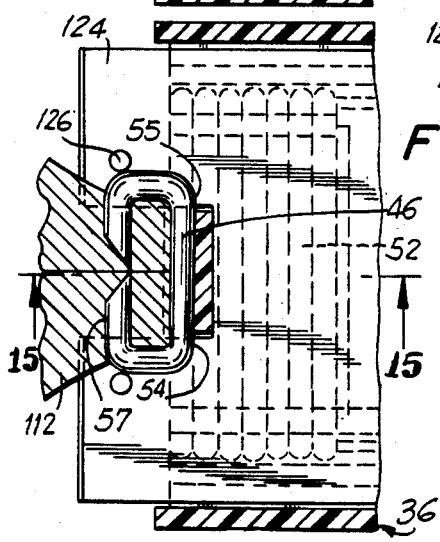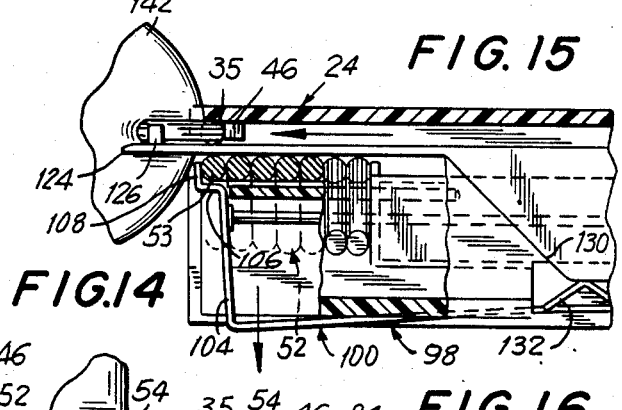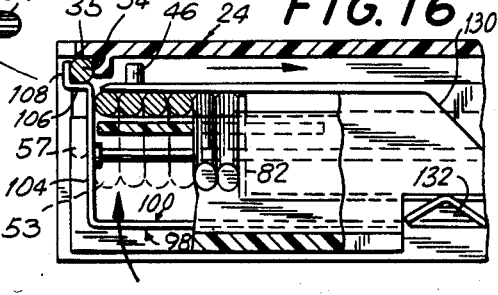

SURGICAL STAPLER

BACKGROUND OF THE INVENTION

This invention relates to a device for the closure of incisions at the conclusion of many typical surgical procedures. Such closures can involve the rejoining of a wide variety of tissue types and bones, such as the rib cage, fascia, muscle, skin and fat. Primary objectives of these closure procedures are to effect rapid and proper healing with a minimum of discomfort and scarring and to ensure that the wound remains securely closed. A related objective is that the closure not interfere with subsequent bandages and change of dressing.

Closure generally involves joining various layers of tissue, each in a special and correct manner. For instance, in abdominal surgery the severed peritoneum layer must be joined, followed by the layers of muscle, fascia, fat and skin. Additionally, retention sutures which pass through all layers may be used or required as insurance that the closure will not open. To accomplish these sutured closures typical materials include silk, gut and a wide variety of synthetics including Dacron ® Teflon ® and various new disposable materials. Depending on the strength required, the material may be monofilament or braided and the caliber may be varied. Also there are metal sutures which are usually made from nonreactive stainless steel. Each material has characteristics which make its use appropriate for a specific purpose.

In all these techniques an important consideration is scar formation, the manner in which the human body reacts to suture materials which behave, for the most part, as foreign bodies and cause the body's defense mechanisms to seal them off with connective tissue. When the body's reaction is greater, more scar tissue will be formed.

Obviously, sutures cannot be passed without a delivery system which for these sutures consists of a large assortment of needles. Each type of needle is designed to provide a particular function, such as ease of handling, ease of passage, ease of release, minimal trauma, etc. The surgeon will generally either thread a needle or use prethreaded suture-needle combinations and secondary instruments such as suture holders.

Wound closure is thus a major concern among surgeons and among the primary objectives of wound closure are: (a) to minimize time required to close, (b) to reduce surgeon fatigue and patient anesthesia time, (c) to reduce tissue trauma and accelerate wound healing, (d) to minimize blood loss, (e) to achieve optimum cosmetic results, and (f) to control and reduce overall costs.

These objectives have led to the development of a relatively new method of closure, namely joining adjacent tissue with metal staples delivered and secured by a staple gun. These metal staples which have partially replaced traditional suture techniques, have become popular for both external and internal closures, including joining cut ends of blood vessels, hollow organs and various layers of tissue within the body. Dozens of stapling devices for surgery have been developed by Americans and others, especially workers in the Soviet Union.

One aspect of virtually all of these known stapling devices is the characteristic way in which they function and the use of bendable but nonresilient metal staples. Force is applied to change the initially open, generally U-shape configuration of each metal staple to a final, closed configuration, so that the staple will hold two adjacent edges of tissue together. The staple devices are held and operated by the surgeon's hand, with force applied either manually by the surgeon or by a power-assisted mechanical force incorporated into the stapler. The force required to bend or crush the ends of the nonelastic metal staples is substantial, and is typically applied by a driver which drives each staple into position and then forcibly bends the legs of the staple. Once placed, the staples cannot be removed without the use of a separate device which forcibly returns the staple to its generally open configuration, so that removal is possible without tearing the tissue.

Broadly, the present invention provides a surgical stapling instrument for joining with staples two opposing layers of tissue, skin and/or fascia of a patient. This invention utilizes a unique delivery system which provides a mode of increased control and includes provision for turning the staple generally normal to the plane of a stack of staples, which are stacked as in a conventional paper stapler, to provide a more efficient and space-saving surgical stapler.

Another object of the present invention is to achieve a reduction in overall size and weight of the stapler in order to provide more exacting control for the surgeon, especially in difficult-to-reach areas.

A further objective is to reduce the amount of manual force and motion applied to the device when it is at the site or delivery point of the staple so that it can be readily used by the surgeon without causing movement.

The present invention is directed toward solving these problems and provides a workable and economical solution to them. The new invention disclosed and claimed in subsequent sections of this application is fundamentally different from all known prior art stapling systems and devices.

SUMMARY OF THE INVENTION

The present invention is a handheld and hand-operated multistage surgical instrument that carries a plurality of new staples, preferably in a cartridge, and delivers and closes one staple at a time to the adjacent edges of an incision being closed or adjacent tissue or other substances being joined. This device is operated by squeezing a trigger a selected distance toward or into the case, and subsequently releasing the trigger to automatically return to its normal position.

One end of an anvil is fixed to the cartridge retaining the stack of staples. The anvil includes a base having a cam follower surface projecting upwardly therefrom, a staple stack retainer surface extending upwardly from the end of the base in abutting relation with the stack of staples preventing horizontal movement of the stack of staples. The anvil also includes a staple transport surface extending generally outwardly from an end of the staple stack retaining surface, and a staple forming surface extending generally upwardly from the end of the staple transport surface.

A staple former slideably advances within the barrel and includes a pair of arms extending outwardly therefrom which impinge upon the legs of the subject staple to turn the staple. In addition, a pair of projections extend upwardly therefrom and engage with the cross-arm of the staple to form the cross-arm during the forming process. Each arm includes a leg retaining edge to retain the staple during stripping from the anvil after forming. The former further includes a cam extending downwardly therefrom which engages with the cam follower surface of the anvil for angular displacement of the anvil.

The former is displaceable between a start position wherein the legs of the staple are generally perpendicular to the plane of the former and generally parallel to the plane of the stack of staples, and an intermediate position wherein the former legs impinge upon the arms of the staple forcing the staple to rotate about the cross-arm of the staple, and a final position wherein the former advances forwardly having the projections engaging the cross-arm of the staple and forming the staple around the staple forming surface of the anvil into a closed gripping configuration for closing and engaging the legs of the staple within the incision or wound.

The anvil is displaceable between a rest position, and a flexed position wherein the former is advanced forwardly and the cam engages the cam follower surface cantilevering downwardly the free end of the anvil thereby disengaging the staple from the anvil and the staple being restrained from movement with the anvil by the leg retaining edges of the former stripping the staple for subsequent discharge. In addition, in the flexed position, the staple transport surface of the anvil is displaced downwardly to thereby receive the leading staple of the stack of staples. The anvil is further displaced to a return position wherein the anvil is cantilevered upwardly transporting the leading staple to a position for sequential stapling of the tissue.

The case includes a plurality of extending tabs and a barrel having a cavity formed circumferentially therein which rotatably engages the tabs of the case permitting rotational detent of the barrel in relation to the case. The cavity also includes a plurality of undulations which frictionally retain the tabs of the case within the cavity and provide for a controllable orientation of the angular position of the barrel relative to the case so that the surgeon may direct the staple to the desired tissue with minimum effort.

The new stapler as disclosed herein has many features which are significant and useful when used in the combination described above or in various other combinations. The new invention comprises first, a surgical stapler system wherein the stack of staples is configured in a typical orientation as those of a paper stapler and further includes a means for transporting, turning and forming the leading staple so that the staple may be discharged perpendicular to the stack of staples. The invention further comprises a delivery system, or apparatus to contain the staples, and to deliver, strip, and load them as required, without having to use a crushing force.

Other objects and advantages of the invention will become apparent from the following detailed description and from the appended drawings in which like numbers have been used to describe like parts of the several views.

BRIEF DESCRIPTION OF THE DRAWINGS

FIG. 2 is a cross-sectional view of the surgical stapler taken along line 2—2 of FIG. 1;

FIG. 3 is a partial top plan view taken along line 3—3 of FIG. 2;

FIG. 10 is a partial top plan view similar to FIG. 3 showing the staple in the turned position;

FIG. 11 is a cross-sectional view taken along line 11—11 of FIG. 10;

FIG. 12 is a partial top plan view similar to FIG. 10 showing the staple in the forming position;

FIG. 13 is a cross-sectional view taken along line 13—13 of FIG. 12;

FIG. 14 is a partial top plan view similar to FIG. 10 showing the staple in the strip-load position;

FIG. 15 is a cross-sectional view taken along line 15—15 of FIG. 14;

FIG. 16 is a partial cross-sectional view similar to the left side of FIG. 3 showing the start or initial retention position of the leading staple.

DESCRIPTION OF THE PREFERRED EMBODIMENT

Figure 1:
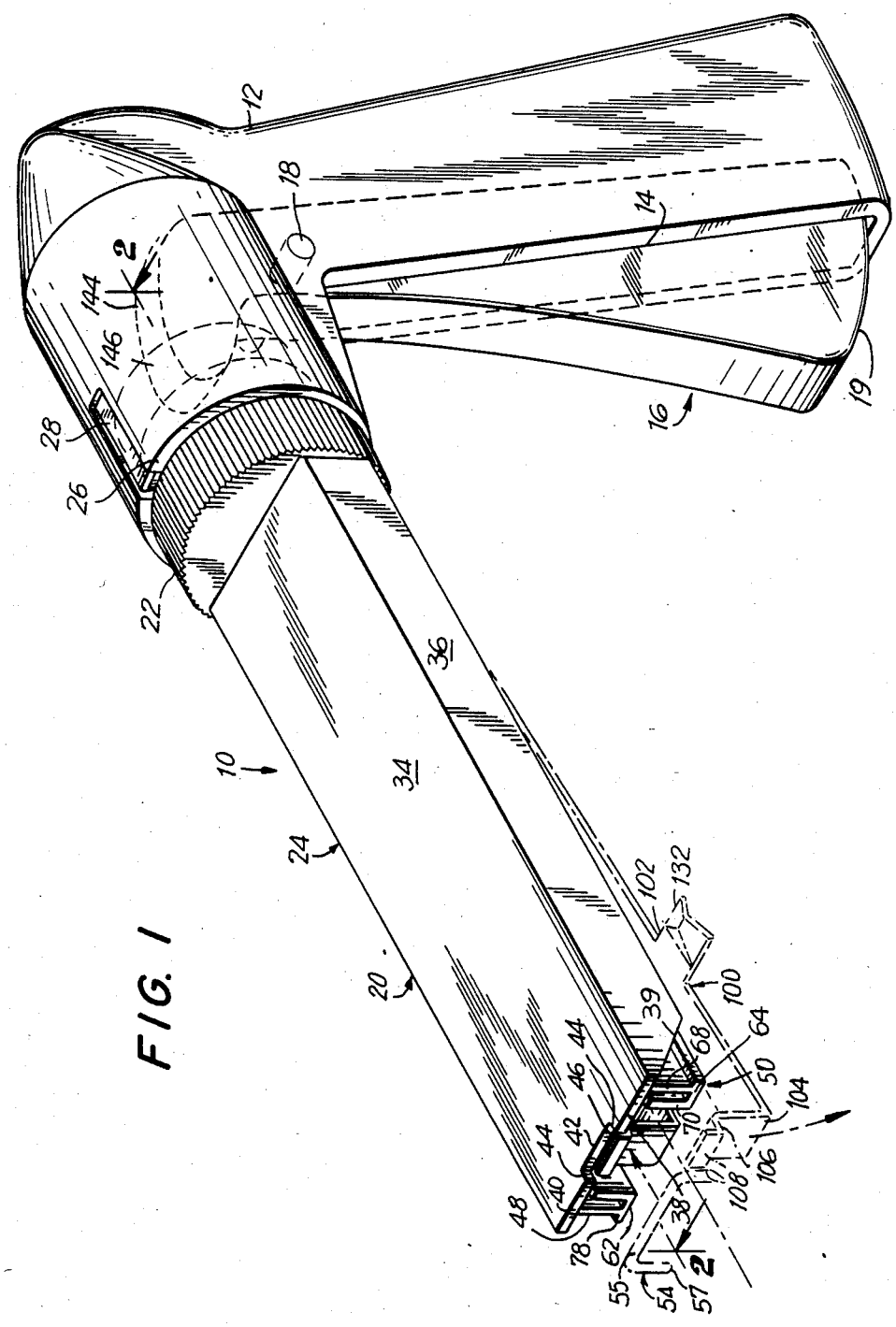
FIG. 1 is a front perspective view of a preferred embodiment of the new surgical stapler of the present invention.

As shown in FIG. 1, a hand-held and hand-operated multistage surgical stapler 10 delivers and closes one staple at a time to the adjacent edges of an incision being closed or adjacent tissue or other substances being joined. Surgical stapler 10 is formed generally of a vertical case 12 having a trigger opening 14 through which a trigger 16 is engageably inserted. Trigger 16 pivots about a trigger pivot point 18 and moves between a first extended position (shown in FIG. 1) and a second retracted position upon hand pressure being applied on the trigger 16 by the surgeon. The bottom 19 of trigger 16 angles upwardly. FIG. 1 illustrates that trigger 16 is pivotable with about 30° of movement.

Figure 9:
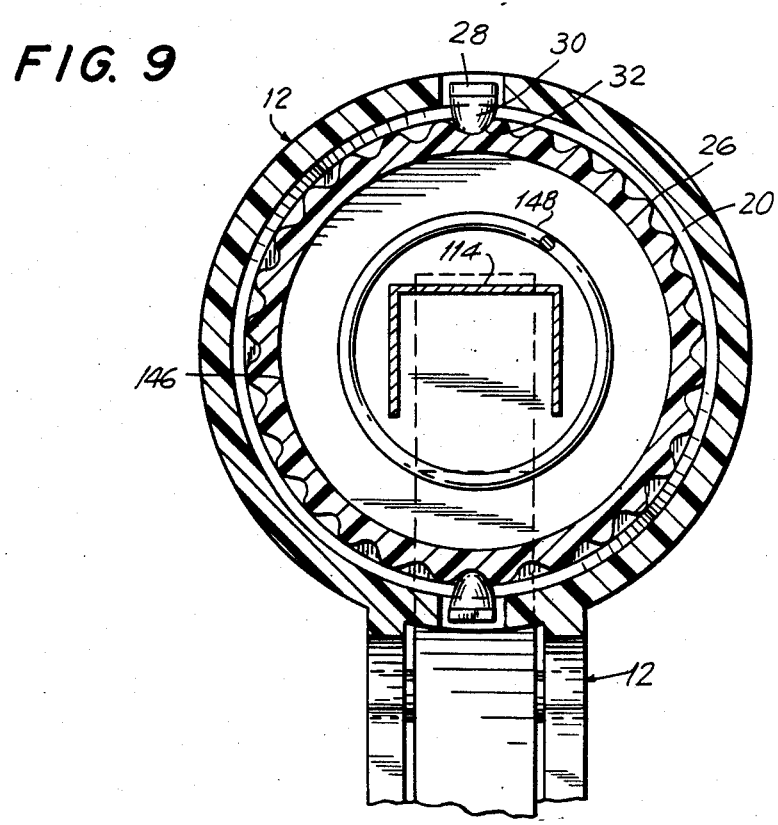
FIG. 9 is a front sectional view taken along line 9—9 of FIG. 2.

The stapler of the present invention also includes a barrel 20 having a cylindrical portion 22 and an upper cartridge housing 24. Cylindrical portion 22 includes a circumferential depression or cavity 26 formed therein, as best shown in FIGS. 3 and 9. Case 12 includes a plurality of tabs 28 extending outwardly therefrom and each tab 28 is provided with a head 30 depending downwardly therefrom. Cavity 26 is rotatably engaged by heads 30 of tabs 28 permitting rotational detent of the barrel 20 in relation to case 12. Cavity 26 also includes a plurality of undulations 32, as best shown in FIG. 9, which provide a controllable orientation of the angular position of barrel 20. The surgeon may specifically direct a staple to the desired tissue as the barrel 20 "locks" at an angular orientation with minimum effort when head 30 is retained within undulation 32. With the present invention, the surgeon has a free hand and need not restrain the barrel 20 from further rotation with his free hand.

Upper cartridge housing 24 of barrel 20 includes a top face 34 and a bottom face or roof 35 and a pair of side faces 36 depending downwardly from the ends of top face 34. Upper cartridge housing 24 terminates in a front face 38 having a top web member 40 provided with a notch 42 for a barrel arch formed centrally therebetween. Notch 42 includes a pair of side faces 44 depending inwardly from top web member 40 of top face 34. The ends of the side faces 36 opposite to the ends connected to top web member 40 are connected to a rear face or lip 46 depending downwardly from the top face 34 of the barrel 20. The front face 38 also includes an inclined portion 39 preferably with a 30° angle between the front face 38 and the bottom of trigger 16. A pair of side web members 48 depend downwardly from the outer ends of top web members 40. Side web members 48 are the free ends of side faces 36 of upper cartridge 24.

Figure 4:
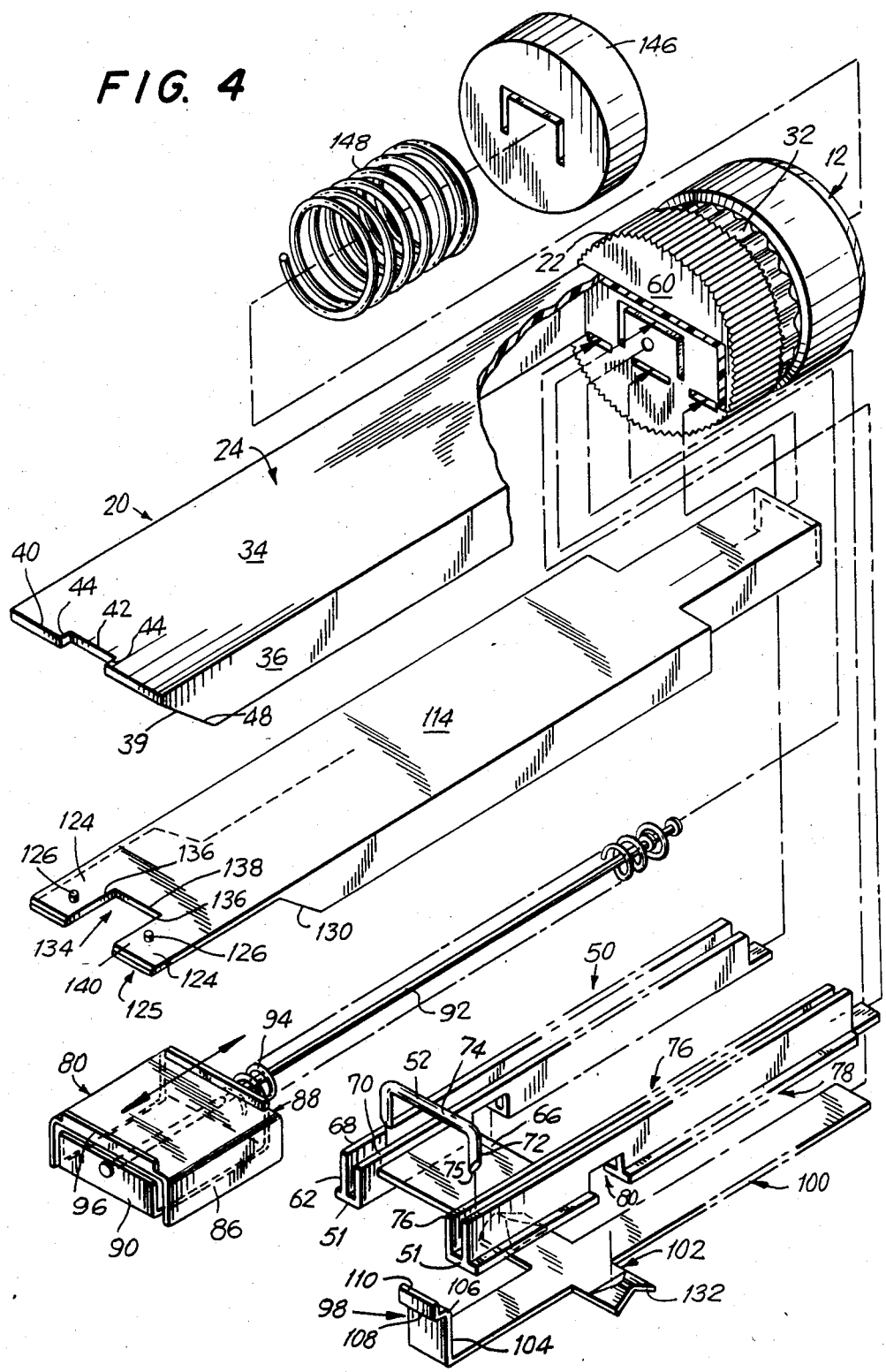
FIG. 4 is an exploded view of the barrel elements of the surgical stapler.

As shown in FIGS. 2 and 3, the forward portion of upper housing 24 of barrel 20 covers a lower cartridge 50, a stack of staples 52, a pusher 82, an anvil 98 and a former 114. Lower cartridge 50 of the present invention, as best shown in FIG. 4, permits the stack of staples 52 to be retained and stacked as in a conventional paper stapler which allows for reasonable manufacturing dimensions and saves critical space in a surgical stapler. The stack of staples 52 includes a first staple 53 and a last or final staple 56. The rear wall 58 of the lower cartridge 50 is connected to the base plate 60 of the barrel 20.

Figure 5:
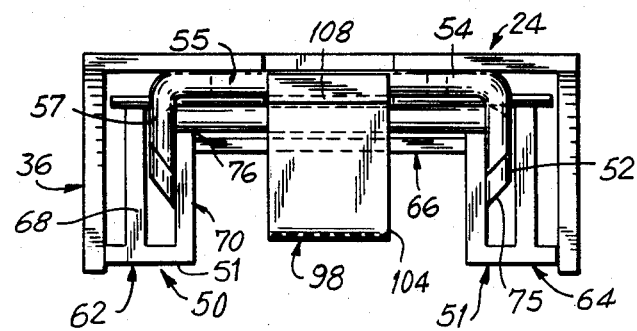
FIG. 5 is a front sectional view taken along line 5—5 of FIG. 2.

Lower cartridge 50 includes a first symmetrical U-shaped channel 62 and a second symmetrical U-shaped channel 64. The first and second U-shaped channels 62 and 64 are connected by middle web members 66 which provides support for channels 62 and 64. Channels 62 and 64 include outer facing legs 68 and inner facing legs 70 with outer facing legs 68 being greater in height than the inner facing legs 70. The legs 72 of stack of staples 52 are inserted between the outer and inner facing legs 68 and 70 and the cross-arms 74 of staples 52 abut and are retained by the top edge 76 of inner facing legs 70. As best shown in FIG. 5, the points 75 of the staples 52 do not contact the floor 51 of lower cartridge 50. This prevents frictional drag of the staples 52 in relation to lower cartridge 50 and permits lower cartridge 50 to be made of plastic or a plastic-like material. The lower cartridge 50 also includes a pair of side flanges 78 extending outwardly from the outer facing legs 70 for abutting engagement with side faces 36 of the upper cartridge 24. The side flanges 78 extend along the entire length of channels 68 and 70 with the exception of a centrally located groove 80.

The present invention also includes a pusher 82 having a top face 84, side faces 86, rear face 88, and a front face 90. A rod 92 is centrally positioned through the pusher assembly 82 and has one end connected to rear face 88 and its free end connected to base plate 60 of barrel 20. Pusher 82 is displaceable between a rear and forward position by a pusher spring 94 disposed about rod 92 which is in biasing relation with rear face 88. Front face 90 of pusher 82 includes an upper extending section 96 which abuts and is adjacent to the last or final staple 56 of the stack of staples 52 being retained within lower cartridge 50.

Figure 6:
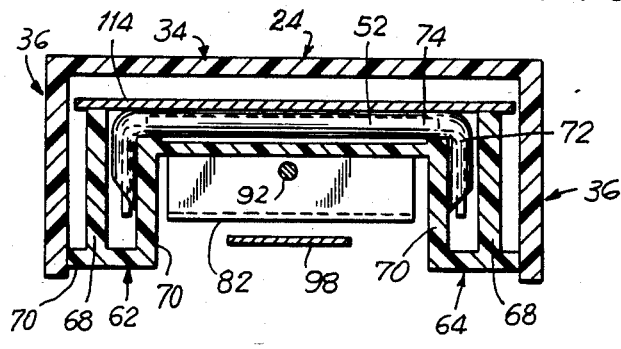
FIG. 6 is a front sectional view taken along line 6—6 of FIG. 2.

Within the surgical stapler assembly 10, an anvil 98 is positioned generally below lower cartridge 50, as shown in FIG. 6, and between first and second U-shaped channels 68 and 70. Anvil 98 includes a base 100 having a pair of side arms 102 extending outwardly therefrom. Side arms 102 are received by and positioned within groove 80 of lower cartridge 50. A staple stack retainer surface 104 extends upwardly from an end of base 100 and retains stack of staples 52 from further movement as a result of the force being applied to the staples 52 by means of pusher 82. The staple stack retainer surface 104 generally abuts the first staple 53 within the stack 52. A staple transport surface 106 extends outwardly from staple stack retainer surface 104 and provides a surface for transporting the first staple 53 from stack 52 to a position where it can be turned and formed. A staple forming surface 108 extends upwardly from the staple transport surface 106 terminating at a free end 110. The staple forming surface 108 provides a surface where the leading staple 54 may be formed around the anvil 98 into a generally square configuration for insertion within the incision or wound 112, see FIGS. 13–15 as well.

The surgical stapler 10 also includes a former 114 positioned within barrel 20 between upper cartridge 24 and lower cartridge 50. Former 114 includes a top face 116, a bottom face 118, a pair of side faces 120 depending downwardly from the lateral edges of top face 116, and terminating in a front face 122. Outer facing legs 68 of lower cartridge 50 engage the bottom face 118 of former 114 retaining former 114 within barrel 20. Top face 116 of former 114 has a pair of arms 124 extending outwardly therefrom. Arms 124 impinge upon the leading staple 54 which is retained by the lip 46 of upper housing 24, bottom face 35 of upper housing 24, staple transport surface 106, and staple forming surface 108 as shown in FIG. 2. Arms 124 provide a means to turn leading staple 54 at least 90°, or normal to the position of the staple in the stack of staples 52 in lower cartridge 50 preferably to insure maximum clarity in the surgeon's line of vision when placing a staple in position. Front face 125 of former 114 is chamfered to aid in rotating the leading staple 54. It is, of course, recognized that an angle less than 90° may still be utilize although an angle less than 90° will not be as beneficial in terms of providing a clear unimpeded sight line to staple placement. As a result of the ability to rotate the staples, the present invention utilizes a stack of staples which are in a conventional paper stapler orientation to reduce the space of the stapler and provide for reasonable manufacturing dimensions.

Figure 7:
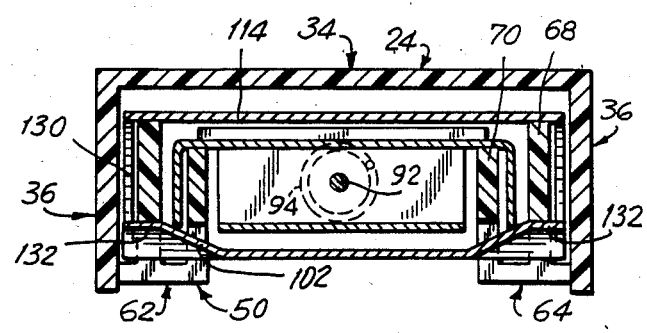
FIG. 7 is a front sectional view taken along line 7—7 of FIG. 2.

A pair of projections 126 extend above the plane of former 114 and into the leading staple 54 and apply a force to the cross-arm 55 of the staple 54 when former 114 is advanced to bend and form the staple around staple forming surface 108 of anvil 98. A cam 130 inclines upwardly along the side faces 120 of former 114. Cam 130 engages a cam follower surface 132 of anvil 98 which extends upwardly from the ends of side arms 102 of anvil 98 when former 114 advances to bend or cantilever downwardly the anvil. The relationship between cam 130 and cam follower 132 is best shown in FIGS. 2, 7, and 15.

An opening 134 is formed between arms 124 of former 114. Opening 134 includes side edges 136 depending inwardly from front face 122 of former 114 and a rear edge 138. The area of arms 124 between projections 126 and each side edge 136 define a leg retaining surface or edge 140.

Bottom face 118 of former 114 tightly abuts the top of the cross arms of the stack of staples 52. Such an arrangement provides for space saving within the surgical stapler 10 and allows leading staple 54 to be inserted within the wound or incision 142 at a greater angle to the tissue to be stapled as the farther the staple is moved upwardly into a position to be turned, the less tilt back angle is allowed with the skin surface for stapling.

A ball 144 of trigger 16 engages a load button 146 which causes former 114 to advance. A first or main spring 148 which is in biasing relation with the load button 146 causes trigger 16 and former 114 to return to their start position.

In use, the present invention is operated by squeezing a pivoting trigger 16 a selected distance toward or into case 12, and subsequently releasing trigger 16 to automatically return it to its rest position. This motion of trigger 16 activates a multi-stage operation that includes the following steps: (a) loading first staple 53 from the stack of staples 52 into staple transport surface 106 of anvil 98, (b) transporting leading staple 54 into a position where it can be turned generally normal to the plane of the stack of staples 52; (c) turning the staple 54 to an orientation generally normal to the incision or wound 90 for subsequent closure and ejection of the leading staple; (d) forming the leading staple 54 around staple forming surface 108 of anvil 98 into a generally square configuration closing legs of leading staple 54 within the incision or wound 142; (e) releasing the staple on a fully controlled basis into the tissue of the wound or incision 142 without having the staple retract with anvil 98; and (f) reloading a new staple into the placement area. Each of these steps will be described in detail below.

FIG. 2 illustrates the leading staple 54 in the starting position. The stack of staples 52 is retained within lower cartridge 50 with legs 72 of the staples depending generally downwardly. The cross-arms 74 of the stack of staples 52 are tightly retained by bottom face 118 of former 114. The pusher 82 upon the urging of pusher spring 94 exerts a force upon the stack of staples 52. The stack of staples 52 is restrained from further movement by staple stack retainer surface 104 of anvil 98.

Figure 8:
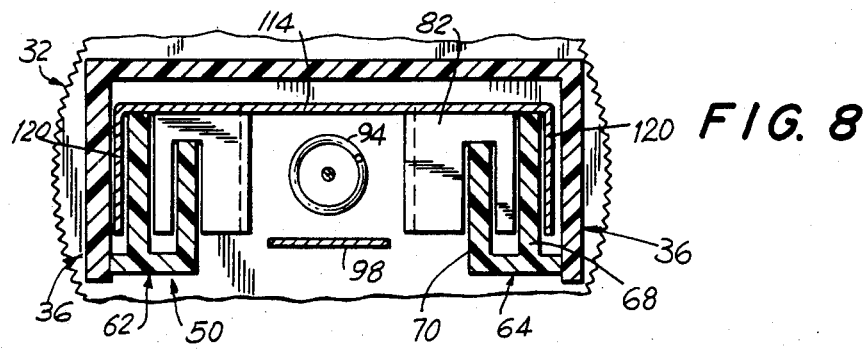
FIG. 8 is a front sectional view taken along line 8—8 of FIG. 2.

As shown in FIGS. 2 and 5, the leading staple 54 in the starting position, has its legs 57 depending generally downwardly generally parallel to legs 72 of the stack of staples 52. As illustrated in FIGS. 2 and 3, leading staple 54 is snugly retained within the opening defined by staple forming surface 108, staple transport surface 106 of anvil 98, downwardly depending lip 46 of upper cartridge 24 and bottom face 35 of upper cartridge 24. Anvil 98 is so formed and installed that in its rest position staple transport surface 106 presses staple 54 against bottom face 35 with moderate force retaining staple 54 snugly within the opening defined by staple transport surface 106, staple forming surface 108, lip 46 and bottom face 35. In the rest position, cam 130 of former 114 is recessed behind cam follower surface 132 of anvil 98 and does not engage cam follower surface 132 as illustrated in FIGS. 2 and 8. Arms 124 of former 114 are adjacent to but do not engage the leading staple 54.

As shown in FIGS. 2 and 10, former 114 is displaceable between a start position as shown in FIG. 2 wherein the legs 57 of leading staple 54 are generally perpendicular to the plane of former 114 and parallel to the plane of the stack of staples 52 and cross-arm 55 of leading staple 54 is reliably retained between staple forming surface 108, staple transport surface 106, bottom face 35, and lip 46, and an intermediate position, as illustrated in FIGS. 10 and 11, wherein legs or arms 124 of former 114 advance forwardly upon actuation of trigger 116 exerting a force upon the load button 146. In the former intermediate position, former arms or legs 124 impinge upon legs 57 of leading staple 54 so that legs 57 are turned upwardly in a plane generally normal to legs 72 in the stack of staples 52 and parallel to the plane of former 114. After being turned or rotated, the leading staple 54 is tightly retained by staple forming surface 108, staple transport surface 106, bottom face 35 and downwardly depending lip 46 of upper cartridge 24, the projections 126 and top face 116 of former 114 as depicted in FIG. 11. The design of this preferred embodiment of the present invention provides better visibility of the closure area since the leading staple 54 is positioned for discharge directly into the wound or incision 142 without any obstacles in the surgeon's line of sight.

FIGS. 12 and 13 illustrate the forming of leading staple 54 within the incision or wound 142. Former 114 advances further forwardly from the intermediate turning position into the final forming position. In the final or forming position, projections 126 of former 114 advance forwardly and apply a force upon cross-arm 55 of the leading staple 54. The staple 54 is formed around staple forming surface 108 of the anvil 98. Leading staple 54 is formed into a generally square configuration wherein legs 57 of staple 54 close adjacent one another within the incision or wound 142. As shown in FIG. 12, the distance between the pair of projections 126 generally defines the length of the formed staple 54. The leading staple 54 is formed in a plane generally perpendicular to the plane of the stack of staples 52 and in a plane generally parallel to the plane of former 114. As illustrated in FIG. 13, the staple in the formed position within the incision or wound 142 is retained within the surgical stapler 10 by staple forming surface 108, staple transport surface 106, bottom face 35, downwardly depending lip 46, and leg retaining surface or edge 140 on top face 116 of former 114. Of course, the leading staple 54 will also be retained by the tissue of the wound or incision 142. In the forming position, the stack of staples 52 still receives a force which is being applied by pusher 82 upon the urging of pusher spring 94 and the stack of staples 52 is restrained from movement by staple stack retainer surface 104.

FIGS. 14, 15, and 16 illustrate the strip-load phase of the surgical stapler 10. As shown in the FIGS. 13 and 15, anvil 98 is displaceable between a rest position, as illustrated in FIG. 13, and a flexed position wherein former 114 is advanced forwardly and cam 130 of former 114 engages cam follower surface 132 of anvil 114 cantilevering or bending downwardly anvil 98 disengaging the leading staple 54 from staple forming surface 108 of anvil 98.

As shown in FIG. 14, the leading staple 54 is restrained from movement downwardly with anvil 98 by leg retaining surface 140 of former 114. The leg retaining edges 140 aid in disengaging and discharging the fully formed leading staple outwardly through the staple discharge area into the wound or incision 142 without allowing the formed leading staple 54 to move downwardly with anvil 98. The leg retaining edges 140 are of extreme importance as the frictional engagement between the leading staple 54 and anvil 98 created by forming the leading staple 54 around staple forming surface 108 creates a frictional attachment of the staple 54 to anvil 98.

As shown in FIG. 15, as the anvil is displaced downwardly, staple transport surface 106 moves downwardly so that it is at a vertical level generally in the plane of cross-arm 74 of first staple 53 within the stack of staples 52. The first staple 53 within the stack of staples 52 is urged forwardly to be retained by staple forming surface 108 and staple transport surface 106 as a result of force applied by pusher 80 upon the stack of staples 52.

As shown in FIGS. 15 and 16, as former 114 retracts and cam 130 disengages cam follower 132, the formed leading staple 54 is positioned within the wound or incision 142. As illustrated in FIG. 16, the anvil 98 is cantilevered or bent upwardly transporting the leading staple 54 upwardly with its legs in a plane generally parallel to plane of the stack of staples 52 as shown in FIG. 2. The leading staple 54 is transported upwardly within the cavity defined by staple forming surface 108 and staple transport surface 106. The leading staple 54 is transported upwardly into the former start position as shown by both FIGS. 2 and 16 wherein the leading staple is retained by staple transport surface 108, staple transport surface 106, and bottom face 35 and downwardly depending lip 46 of the upper cartridge 24.

Flex tabs 28 extending outwardly from case 12 are rotatably engageable within the cavity 26 of the barrel 20 permitting rotational detent of the barrel 20 in relation to the case 12. Because cavity 26 includes a plurality of undulations 32, the surgeon may direct the staple to the desired tissue with minimum effort as the tabs 28 are frictionally retained within an undulation 32 to thereby provide a controllable orientation of the angular position of the barrel 20 relative to the case 12.

The main or former spring 148 opposes the action of trigger 16. Main or former spring 148 returns former 114 to its start position and returns trigger 16 to its first retracted position. Pusher spring 94 urges pusher 82 forwardly applying a force on the stack of staples 52 so that each sequential staple may be received by staple transport surface 106 of anvil 98 when anvil 98 is cantilevered downwardly.

As shown herein, all functions of the device (turning, forming, stripping, and loading) are accomplished as part of a continuous mechanical action. The present invention allows the manufacturing of a surgical stapler wherein the stack of staples 52 is configured in a typical orientation as those of a conventional paper stapler. The present invention also includes a means for transporting, turning, stripping and forming the leading staple so that the staple may be directed perpendicular to the tissue to be closed.

To produce the proper movement pattern of parts for turning, forming, stripping, and loading of the staples, many different mechanisms may be devised; however, the preferred embodiment disclosed herein is not only remarkably simple to manufacture and use, it is designed to be extremely inexpensive to produce, while still meeting all the objectives described in early paragraphs.

While the preferred embodiment of the present invention has been described, it should be understood that various changes, adaptations and modifications may be made therein without parting from the spirit of the invention and the scope of the appended claims.

We claim:

1. A stapling device for use in ejecting a single staple to close an incision or wound comprising:
    a barrel having a bottom and a top side and a staple discharge area,
    a cartridge assembly adapted to receive a plurality of staples in the form of a stack disposed wihtin said barrel,
    a pusher assembly engageable with said stack of staples and movable between a first rearward position and a second forward position to advance said stack of staples,
    a control means for turning a single staple of the stack of staples to be ejected from a first position to a second position at a significant angle to said first position at a vertical plane other than the vertical plane of the stack of staples,
    forming means for forming the staple into a closed gripping configuration, said forming means including an anvil having a staple transport surface upon which said staple is transported and a staple forming surface extending generally upwardly from said staple transport surface; and a former engageable with the cross-arm of the staple to be ejected to cooperate with means to restrain said staple and displaceable between an intermediate position wherein said staple is unformed and in its plane of ejection and a final position wherein said staple is formed within the incision in a closed gripping configuration, and
    stripping means for disengaging the staple to be ejected from said device and to eject the fully formed staple.

2. The stapling device according to claim 1 wherein said control means rotates the staple generally normal to the plane of the stack of staples.

3. The stapling device according to claim 1 wherein said control means includes:
    an anvil having a staple transport surface upon which the staple is transported and a staple forming surface extending generally upwardly from said staple transport surface; and
    a former engageable with the legs of said staple to be ejected and cooperable with means to restrain said staple and displaceable between a first position wherein said staple is in its initial plane of orientation and an intermediate position wherein said staple is rotated to its plane of ejection.

4. The stapling device according to claim 3 wherein said former includes a chamfered edge which aids in the rotation of the staple.

5. The stapling device according to claim 2 wherein said former includes a bottom face abutting the staples within said cartridge allowing the staple to be inserted in the incision when the stapler is at a significant tilt-back angle from a generally normal position with respect to the incision.

6. The stapling device according to claim 3 wheien said former includes a pair of arms which impinge upon the legs of the staple to rotate the staple to its plane of ejection when said former is advanced to its intermediate position.

7. The device according to claim 3 wherein said means to restrain said staple includes said bottom side of said barrel and a lip depending downwardly from said bottom side cooperating with said staple transport surface and said staple forming surface to restrain said staple.

8. The staple device according to claim 3 wherein said former includes a pair of projections extending upwardly therefrom which cooperate with said staple forming surface and said staple transport surface to reliably retain the staple in the former advanced position.

9. The stapling device according to claim 1 wherein said former includes a pair of projections extending upwardly therefrom engaging said cross-arm of said staple for forming said staple.

10. The stapling device according to claim 9 wherein said projections cooperate with said staple forming surface to form said staple around said staple forming surface into a closed gripping configuration.

11. The stapler device according to claim 1 wherein the stripper means comprises:

a former including a cam extending downwardly therefrom and a means to retain said formed staple;

an anvil having a base, a cam follower surface projecting upwardly from said base, a staple stack retainer surface extending upwardly from an end of said base; a staple transport surface extending generally outwardly from an end of said staple stack retainer surface upon which said plurality of staples are transported; and said anvil displaceable between a rest position and a flexed position wherein said staple is disengaged from said staple forming surface as said anvil is pivoted downwardly and restrained from downward movement with said anvil by said means to restrain said formed staple.

12. The stapler device according to claim 11 wherein said means to restrain said formed staple including a pair of arms extending downwardly from said former having leg retainer edges, said leg retainer edges restrain movement of the staple downwardly when said anvil is displaced to its flexed position.

13. The stapler device according to claim 11 wherein said cam engages said cam follower when said former is advanced forwardly to cantilever downwardly said anvil to disengage the staple from said staple forming surface.

14. The stapler device according to claim 1 and further includes:

a loading means for loading a single staple within a stack of staples into a position to be turned.

15. The stapler device according to claim 1 and further including a case engageable with said barrel providing for hand gripping of the device.

16. The stapler device according to claim 15 and further including a trigger pivotable between a first and a second position for manual actuation of the device.

17. The stapler device according to claim 16 and further including a load button in engageable with said trigger and in juxtaposition to said control means.

18. The stapler device according to claim 17 and further including a first main spring in biasing engagement with said load button displacing said control means.

19. The stapler device of claim 1 wherein said cartridge includes first and second U-shaped channels each having an inner facing and outer facing leg, the stack of staples rest upon said inner facing legs.

20. The stapler device of claim 1 wherein said cartridge includes a floor which does not contact the stack of staples.

21. The stapler device of claim 1 wherein said cartridge is made from a plastic or plastic-like material.

22. A stapling device for use in ejecting a single to close an incision or wound comprising:

a barrel including a staple discharge area, said barrel including a roof and a lip depending downwardly from said roof;

a cartridge assembly adapted to receive a plurality of staples in a generally planar arrangement disposed within said barrel;

a pusher assembly engageable with said stack of staples and movable between a first rearward position and a second forward position to advance said stack of staples;

a control means for turning a single staple around an axis generally normal to the plane of the stack of staples at a vertical plane other than the vertical plane of the stack of staples, said control means including an anvil having a staple transport surface and a staple forming surface extending generally upwardly from said staple transport surface, and a former including a pair of arms which impinge upon the legs of the staple and is displaceable between a start position wherein the legs of the staple are generally perpendicular to the plane of the former and the cross-arm of the staple is reliably retained between said staple forming surface, said staple transport surface, said lip, and said roof, and an intermediate position, wherein said legs of said former impinge upon the arms of the staple forcing the staple to rotate generally perpendicular to the plane of the stack of staples, said former also including a pair of projections extending upwardly therefrom which cooperate with said staple forming surface and said staple transport surface to reliably retain the staple in the former advanced position, forming means for forming the staple into a closed gripping configuration;

stripping means for disengaging the staple to be ejected from said device; and loading means for loading a single staple within said stack of staples into a position to be turned.

23. The stapling device according to claim 22 wherein said stripper means comprises:

an anvil having a base; a cam follower surface projecting upwardly from said base; a staple stack retainer surface extending upwardly from an end of said base; a staple transport surface extending generally outwardly from an end of said staple stack retainer surface; and a staple forming surface extending generally upwardly from an end of said staple transport surface;

a former including a cam extending downwardly therefrom; a pair of projections extending upwardly therefrom, a pair of arms extending outwardly therefrom and having leg retaining edges; and said anvil displaceable between a rest position and a flexed position wherein said former is advanced forwardly by said cam engaging said cam follower surface cantilevering downwardly said anvil to disengage the staple from said staple forming surface and said leg retaining edges restraining the staple from downward movement with said anvil.

24. The stapling device according to claim 22 and further including load button engageable with said trigger and in juxtaposition to said former.

25. The stapling device according to claim 24 and further including a former spring means in biasing engagement with said load button to return said trigger to its first position and return said former to its rest position.

26. The stapling device according to claim 24 and further including a former spring means in biasing engagement with said load button and capable of displacing said former between said intermediate and final positions.

27. The stapling device according to claim 22 wherein said former includes a chamfered edge aiding in rotating the staple.

28. The stapling device according to claim 22 wherein said cartridge includes a floor which does not contact the stack of staples.

29. The stapling device according to claim 22 wherein said cartridge is made from plastic or a plastic-like material.

30. A stapling device for use in ejecting a signle staple to close an incision or wound comprising:
- a barrel having a bottom and a top side and a staple discharge area,
- a cartridge assembly adapted to receive a plurality of staples in the form of a stack disposed within said barrel,
- a pusher assembly engageable with said stack of staples and movable between a first rearward position and a second forward position to advance said stack of staples,
- a control means for turning a single staple of the stack of staples to be ejected from a first position to a second position at a significant angle to said first position at a vertical plane other than the vertical plane of the stack of staples,
- forming means for forming the staple into a closed gripping configuration,
- stripping means for disengaging the staple to be ejected from said device and to eject the fully formed staple, and
- a loading means for loading a single staple within a stack of staples into a position to be turned, said loading means including:
- a means for advancing said stack of staples;
- an anvil having a base; a cam follower surface projecting upwardly from said base; a staple stack retainer surface extending upwardly from an end of said base; a staple transport surface extending generally outwardly from an end of said staple stack retainer surface; a staple forming surface extending generally upwardly from an end of said staple transport surface;
- a former including a means for engaging said cam follower surface;
- said anvil displaceable between a flexed position wherein said means for engaging said cam follower engages said cam follower so that said staple transport surface receives the leading staple of the stack of staples and a return position wherein said staple is moved upwardly into a position to be turned.

31. The stapler device according to claim 30 wherein said means for advancing said stack of staples is a pusher spring means for displacing said pusher between its rearward and forward positions.

32. The stapler device according to claim 30 wherein said means for engaging said cam follower surface includes a cam extending downwardly from said former.

33. The stapler device according to claim 30 wherein said staple stack retainer surface prevents forward horizontal movement of the stack of staples in said anvil return position.

34. A stapling device for use in ejecting a single staple to close an incision or wound comprising:
- a barrel having a bottom and a top side and a staple discharge area, and also including a cavity circumferentially formed therein,
- a case engageable with said barrel providing for hand-gripping of the device,
- a trigger pivotable between a first and a second position for manual actuation of the device,
- a plurality of tabs extending outwardly from said case rotatably engaging said cavity to permit rotational detent of said barrel in relation to said case,
- a cartridge assembly adapted to receive a plurality of staples in the form of a stack disposed within said barrel,
- a pusher assembly engageable with said stack of staples and movable between a first rearward position and a second forward position to advance said stack of staples,
- a control means for turning a single staple of the stack of staples to be ejected from a first position to a second position at a significant angle to said first position at a vertical plane other than the vertical plane of the stack of staples,
- forming means for forming the staple into a closed gripping configuration, and
- stripping means for disengaging the staple to be ejected from said device and to eject the fully formed staple.

35. The stapling device according to claim 34 wherein said cavity includes a plurality of undulations to frictionally retain said tabs within said cavity providing a controllable orientation of the angular position of said barrel relative to said case.

36. A stapling device for use in ejecting a single staple to close an incision or wound comprising:
- a barrel including a staple discharge area;
- a cartridge assembly adapted to receive a plurality of staples in a generally planar arrangement disposed within said barrel;
- a pusher assembly engageable with said stack of staples and movable between a first rearward position and a second forward position to advance said stack of staples;
- a control means for turning a single staple around an axis generally normal to the plane of the stack of staples at a vertical plane other than the vertical plane of the stack of staples;
- forming means for forming the staple into a a closed gripping configuration; said forming means including an anvil having a staple transport surface and a staple forming surface extending upwardly from said staple transport surface; and a former including a pair of projections extending upwardly from said staple transport surface; and a former including a pair of projections extending upwardly therefrom and displaceable between an intermediate position wherein the staple is tensionably retained generally parallel to said former by said projections, said staple forming surface and said staple transport surface, and a final position wherein said former advances forwardly with said projections engaging the cross-arm of the staple and forming the staple around said staple forming surface into a closed gripping configuration within the incision or wound,
- stripping means for disengaging the staple to be ejected from said device; and
- loading means for loading a single staple within said stack of staples into a position to be turned.

37. A stapling device for use in ejecting a single staple to close an incision or wound comprisng:
- a barrel including a staple discharge area; said barrel includes a roof and a lip depending downwardly from said roof;

a cartridge assembly adapted to receive a plurality of staples in a generally planar arrangement disposed within said barrel;

a pusher assembly engageable with said stack of staples and movable between a first rearward position and a second forward position to advance said stack of staples;

a control means for turning a single staple around an axis generally normal to the plane of the stack of staples at a vertical plane other than the vertical plane of the stack of staples;

forming means for forming the staple into a closed gripping configuration;

stripping means for disengaging the staple to be ejected from said device; and loading means for loading a single staple within said stack of staples into a position to be turned, said loading means including:

an anvil having a base; a cam follower surface projecting upwardly from said base; a staple stack retaining surface extending upwardly from an end of said base; a staple transport surface extending generally outwardly from an end of said staple stack retainer surface; and a staple forming surface extending generally upwardly from an end of said staple transport surface;

a former including a cam extending downwardly therefrom;

a pusher spring means for displacing said pusher between its rearward and forward positions and tensionally retaining the stack of staples adjacent said staple stack retaining surface; and said anvil being displaceable between a flexed position, wherein said cam engages said cam follower surface cantilevering downwardly said anvil so that said staple transport surface receives the staple from the stack of staples, and a return position moving the staple within said anvil to a position to be turned and formed for sequential stapling of the incision.

38. The stapling device according to claim 37 wherein said staple stack retainer surface prevents forward horizontal movement of the stack of staples in said anvil return position.

39. The stapling device according to claim 37 wherein the former includes a bottom face which abuts the stack of staples within said cartridge thereby allowing the staple to be inserted into the incision when the stapler is at a significant tilt-back angle from a generally normal position with respect to the incision.

40. A stapling device for use in ejecting a single staple to close an incision or wound comprising:

a barrel including a staple discharge area and a cavity circumferentially formed therein;

a case engageable with said barrel providing for hand gripping of the device;

a plurality of tabs extending outwardly from said case engaging said cavity to permit rotational detent of said barrel in relation to said case;

a cartridge assembly adapted to receive a plurality of staples in a generally planar arrangement disposed within said barrel;

a pusher assembly engageable with said stack of staples and movable between a first rearward position and a second forward position to advance said stack of staples;

a control means for turning a single staple around an axis generally normal to the plane of the stack of staples at a vertical plane other than the vertical plane of the stack of staples;

forming means for forming the staple into a closed gripping configuration;

stripping means for disengaging the staple to be ejected from said device; and loading means for loading a single staple within said stack of staples into a position to be turned.

41. The stapling device according to claim 40 wherein said cavity includes a plurality of undulations frictionally retaining said tabs within said cavity providing a controllable orientation of the angular position of said barrel relative to said case.

* * * * *